United States Patent
Yu et al.

(10) Patent No.: US 12,029,477 B2
(45) Date of Patent: Jul. 9, 2024

(54) SYSTEMS, DEVICES, AND RELATED METHODS FOR LASER LITHOTRIPSY

(71) Applicant: Boston Scientific Scimed, Inc., Maple Grove, MN (US)

(72) Inventors: Honggang Yu, San Jose, CA (US); Rongwei Jason Xuan, Fremont, CA (US); Jian Zhang, Santa Clara, CA (US); Charles Alexander Ikan Burdan, San Jose, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 91 days.

(21) Appl. No.: 16/527,962

(22) Filed: Jul. 31, 2019

(65) Prior Publication Data

US 2019/0350654 A1    Nov. 21, 2019

Related U.S. Application Data

(63) Continuation of application No. 15/675,331, filed on Aug. 11, 2017, now Pat. No. 10,405,923.
(Continued)

(51) Int. Cl.
*A61B 18/22* (2006.01)
*A61B 18/20* (2006.01)
(Continued)

(52) U.S. Cl.
CPC .............. *A61B 18/22* (2013.01); *A61B 18/24* (2013.01); *A61B 18/26* (2013.01);
(Continued)

(58) Field of Classification Search
CPC ......... A61B 18/22; A61B 18/24; A61B 18/26; A61B 2018/2244; A61B 2018/2222;
(Continued)

(56) References Cited

U.S. PATENT DOCUMENTS 4,608,979 A    9/1986  Breidenthal et al.
4,620,545 A    11/1986 Shene et al.
(Continued)

FOREIGN PATENT DOCUMENTS

JP     2015097664 A  *  5/2015  ........... A61B 18/245
KR     20160057121 A  *  5/2016
WO     WO 2016/049160 A1   3/2016

OTHER PUBLICATIONS

"Designing UV-Curable Materials For High Temperature Optical Fiber Applications" (M. Ellison et al., PCI Mag, Apr. 1, 2008) (Year: 2008).*

(Continued)

*Primary Examiner* — Erin M Piateski
*Assistant Examiner* — Ranjani Mari Sundaresan
(74) *Attorney, Agent, or Firm* — Seager, Tufte & Wickhem, LLP

(57) ABSTRACT

In one aspect of the present disclosure, a laser fiber may include an optical fiber. The optical fiber may include a proximal portion. The optical fiber also may include a distal portion having a distal end. The optical fiber may be configured to transmit laser energy from the proximal portion to the distal portion for emission of the laser energy from the distal end. The optical fiber also may include a distal tip surrounding the distal portion to protect the distal portion. The distal tip may include a sheet glass material having a laser energy emitting surface. The laser energy emitting surface may be defined by a chemically-strengthened surface layer.

20 Claims, 6 Drawing Sheets

Related U.S. Application Data

(60) Provisional application No. 62/374,411, filed on Aug. 12, 2016.

(51) Int. Cl.
*A61B 18/24* (2006.01)
*A61B 18/26* (2006.01)

(52) U.S. Cl.
CPC ............ *A61B 2018/20553* (2017.05); *A61B 2018/2222* (2013.01); *A61B 2018/2244* (2013.01)

(58) Field of Classification Search
CPC .............................. A61B 2018/20553; A61B 9/008–2009/00897; A61B 606/04–06; A61B 606/10–12
See application file for complete search history.

(56) References Cited

U.S. PATENT DOCUMENTS

| | | | |
|---|---|---|---|
| 5,152,768 A | 10/1992 | Bhatta | |
| 5,231,684 A | 7/1993 | Narciso | |
| 5,425,735 A | 6/1995 | Rosen et al. | |
| 5,509,917 A | 4/1996 | Cecchetti et al. | |
| 5,825,958 A * | 10/1998 | Gollihar | A61C 1/0046 385/125 |
| 6,096,065 A | 8/2000 | Crowley | |
| 6,102,905 A | 8/2000 | Baxter | |
| 6,324,418 B1 | 11/2001 | Crowley et al. | |
| 6,491,685 B2 | 12/2002 | Visuri et al. | |
| 6,726,681 B2 | 4/2004 | Grasso, III et al. | |
| 7,090,411 B2 * | 8/2006 | Brown | G02B 6/4296 385/78 |
| 7,463,801 B2 | 12/2008 | Brekke et al. | |
| 8,073,297 B2 | 12/2011 | Griffin | |
| 8,724,941 B2 | 5/2014 | Reever | |
| 8,861,907 B2 | 10/2014 | Zerfas et al. | |
| 8,870,858 B2 * | 10/2014 | Zerfas | A61B 18/22 606/15 |
| 9,678,275 B1 * | 6/2017 | Griffin | G02B 6/262 |
| 2001/0026666 A1 | 10/2001 | Ferrera et al. | |
| 2007/0292087 A1 * | 12/2007 | Brown | G02B 6/4292 385/92 |
| 2008/0247714 A1 * | 10/2008 | Nakamura | G02B 6/2551 385/96 |
| 2011/0098528 A1 * | 4/2011 | Lewinsky | G02B 6/3624 600/104 |
| 2014/0005647 A1 * | 1/2014 | Shuffler | A61M 25/0136 29/592.1 |
| 2014/0286617 A1 | 9/2014 | Asselin et al. | |
| 2014/0336637 A1 | 11/2014 | Agrawal et al. | |
| 2016/0022295 A1 | 1/2016 | Mantell | |
| 2016/0081749 A1 * | 3/2016 | Zhang | A61B 18/26 606/15 |

OTHER PUBLICATIONS

"Numerical analysis of temperature distributions in Yb-doped double-clad fiber lasers with consideration of radiative heat transfer," Yan et al., Optical Engineering 45(12) 124201 (Dec. 2006) (Year: 2006).*

Boyd et al., "CO2 laser-fabricated cladding light strippers for high-power fiber lasers and amplifiers," Applied Optics, 2016, 55(11), p. 2915-2920 (published Apr. 6, 2016).

Joe Zhou et al. "Optical Fiber Tips and Their Applications" Polymicro Technologies, (5 pages).

* cited by examiner

SYSTEMS, DEVICES, AND RELATED METHODS FOR LASER LITHOTRIPSY

CROSS-REFERENCE TO RELATED APPLICATIONS

This application is a continuation application of prior U.S. patent application Ser. No. 15/675,331, filed on Aug. 11, 2017, which claims the benefit of priority from U.S. Provisional Application No. 62/374,411, filed on Aug. 12, 2016, the entireties of all of which are incorporated by reference herein.

TECHNICAL FIELD

Various aspects of the present disclosure relate generally to treating subjects using lasers. More specifically, the present disclosure relates to systems, devices, and related methods for laser lithotripsy.

BACKGROUND

Lasers have been used in, for example, urology, neurology, otorhinolaryngology, general anesthetic ophthalmology, dentistry, gastroenterology, cardiology, gynecology, thoracic, and orthopedic procedures. More specifically, these procedures may entail the delivery of laser energy as part of treatment protocols. One example of a procedure that may be performed using a laser is lithotripsy. Lithotripsy involves treating a subject's kidneys, ureters, or bladder by removing material therein, such as calculi or stones. Laser lithotripsy is a subset of lithotripsy where laser energy is applied to break down the material, thereby facilitating removal of the material. In one exemplary laser lithotripsy procedure, a laser fiber may be inserted through the working channel of an introducer, such as an endoscope, to the targeted material. The laser fiber may emit laser energy at the targeted material to break down the targeted material into pieces. The pieces may be washed out of, or otherwise removed from, the subject.

The laser fiber may be placed in contact with, or nearly in contact with, the targeted material prior to the application of the laser energy. The targeted material may, in some instances, be in contact with water. Since the water also may absorb the laser energy, the water may be affected by the laser energy intended for the targeted material. For example, the laser energy absorbed by the water may produce shockwaves in the water. The shockwaves may damage the laser fiber. Such damage may reduce the amount of laser energy emitted from the laser fiber. Fixing the damage by, for example, cleaving the damaged portion of the laser fiber, and then re-inserting the laser fiber into subject to continue with a procedure, may increase the time and cost associated with performing the procedure.

Another challenge associated with laser lithotripsy is that differently sized laser fibers may be used, with the laser fiber size being selected based on the location of the targeted material in the subject. For example, a laser fiber having a smaller core size may be selected to reach material in a subject's lower kidney pole. One reason for this selection is that the laser fiber with the smaller core size may be bent to form a tighter curve than an laser fiber having a larger core size, making it easier to maneuver the laser fiber with the smaller core size into the target area. The laser fiber having the smaller core size may, however, be used with the same laser generator as the laser fiber having the larger core size. If the core size of the laser fiber is smaller than that of focused laser energy generated by the laser generator, and/or if the focused laser energy delivered from the laser generator to the core is misaligned or greater than the optical fiber's acceptance angle, errant laser energy may be transferred to components outside of the core, possibly damaging those components and negatively impacting the performance of the laser fiber.

Solutions that can deliver laser energy to targeted material, while reducing or eliminating the occurrence of the above-described drawbacks, may lead to better outcomes for users and subjects.

SUMMARY

Aspects of the disclosure relate to, among other things, systems, devices, and related methods for laser lithotripsy. Each of the aspects disclosed herein may include one or more of the features described in connection with any of the other disclosed aspects.

In one aspect of the present disclosure, a laser fiber may include an optical fiber. The optical fiber may include a proximal portion. The optical fiber also may include a distal portion having a distal end. The optical fiber may be configured to transmit laser energy from the proximal portion to the distal portion for emission of the laser energy from the distal end. The optical fiber also may include a distal tip surrounding the distal portion to protect the distal portion. The distal tip may include a sheet glass material having a laser energy emitting surface. The laser energy emitting surface may be defined by a chemically-strengthened surface layer.

Aspects of the laser fiber may include one or more of the features below. The laser energy emitting surface may be a distal-facing surface. The sheet glass material also may include a proximal-facing surface that faces the distal end of the distal portion of the optical fiber. The distal tip may include a tubular member concentrically surrounding the distal portion of the optical fiber. The tubular member may include a passage that receives the distal portion of the optical fiber. The tubular member may have a distal end opening. The distal end opening may be covered by the sheet glass material. The sheet glass material may be coupled to the tubular member by an epoxy. The tubular member may be coupled to the optical fiber by an epoxy. A proximal end of the tubular member may taper down in a proximal direction. A lens member may be located between the distal end of the optical fiber and the sheet glass material. The lens member may include a gradient index lens. The gradient index may be configured to focus the laser energy. The sheet glass material may include a tubular portion concentrically surrounding the distal portion of the optical fiber. A distal end face of the optical fiber may have a curvature.

In another aspect of the present disclosure, a laser fiber may include an optical fiber. The optical fiber may include a proximal portion. The optical fiber also may include a distal portion having a distal end. The optical fiber may be optically transmissive to transmit laser energy from the proximal portion to the distal portion for emission of the laser energy from the distal end. The optical fiber also may include a distal tip surrounding the distal portion. The distal tip may include a sheet glass material having a laser energy emitting surface. The laser energy emitting surface may be stronger than the distal end of the optical fiber.

Aspects of the laser fiber may include one or more of the features below. The distal tip may include a tubular member concentrically surrounding the distal portion of the optical fiber. The sheet glass material may cover a distal end of the tubular member. The sheet glass material may be stronger than material forming the tubular member.

In another aspect of the present disclosure, a laser fiber may include an optical fiber configured to transmit energy. The optical fiber may include a core. The optical fiber also may include cladding concentrically surrounding at least a portion of the core. The optical fiber also may include a distal portion including a covering concentrically surrounding the cladding. The optical fiber also may include a proximal portion free of the covering. At least a portion of the cladding at the proximal portion may be diffused. The laser fiber also may include a connector configured to couple the optical fiber to a laser generator. The connector may include a tubular member having a passage that receives the proximal portion of the optical fiber. The connector also may include a holder having a passage that (i) receives the tubular member, such that the holder concentrically surrounds a portion of the tubular member, and (ii) receives the distal portion of the optical fiber. The connector also may include a coupler concentrically surrounding the tubular member, the diffused cladding allowing laser energy in the cladding to leave the optical fiber and convert into heat energy within the tubular member, with at least some of the heat energy being dissipated by the tubular member, holder, and coupler before reaching the distal portion of the optical fiber.

Aspects of the laser fiber may include one or more of the features below. A first epoxy may couple the distal portion of the optical fiber to the holder. A second epoxy may couple the holder to the coupler. The first epoxy may have a lower thermal conductivity than the second epoxy.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the present disclosure and together with the description, serve to explain the principles of the disclosure.

DETAILED DESCRIPTION

The present disclosure is drawn to systems, devices, and methods for laser lithotripsy. Reference will now be made in detail to aspects of the present disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the patient. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−5% of a stated value.

Figure 1:
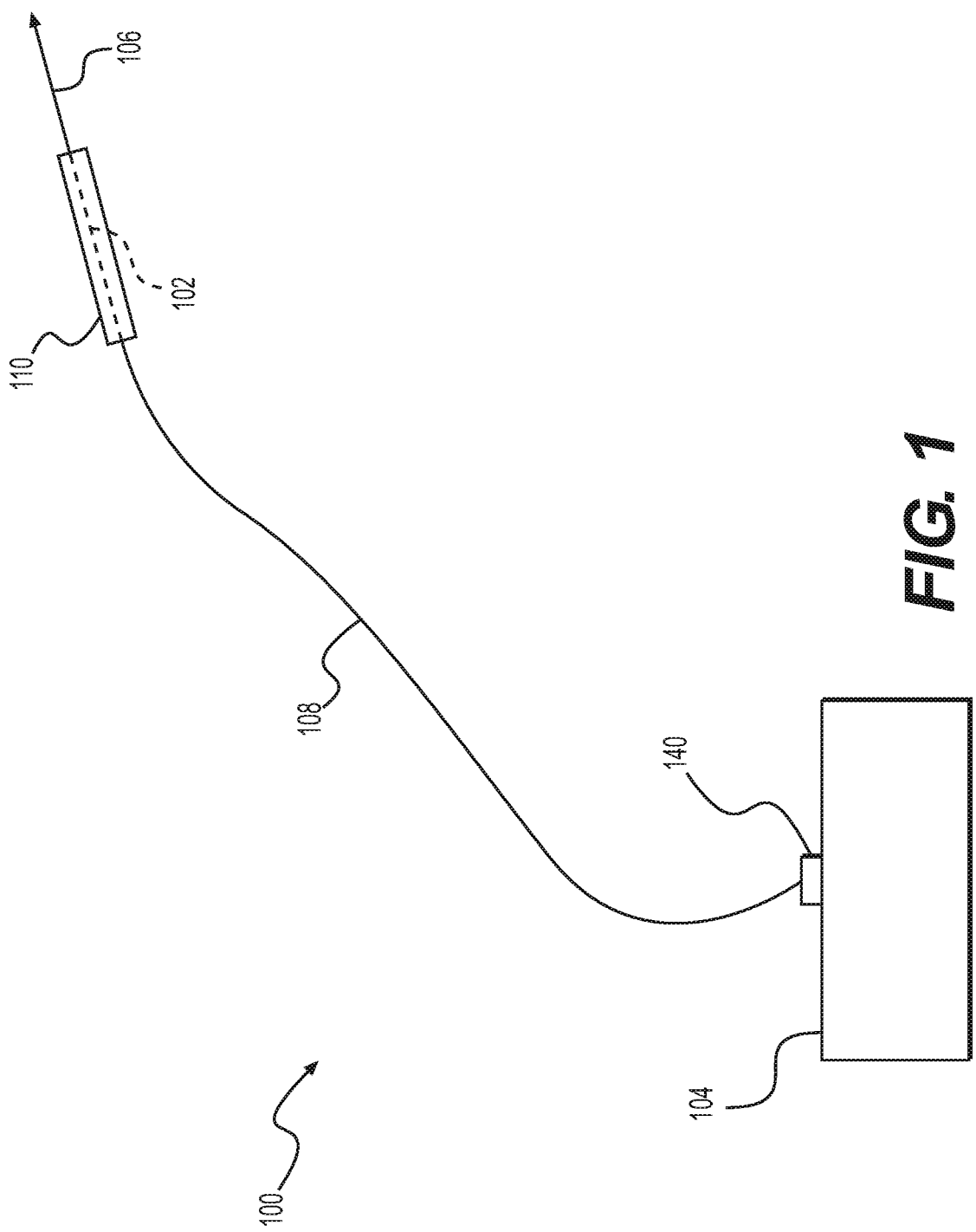
FIG. 1 shows a schematic diagram of a system for laser lithotripsy, in accordance with aspects of the present disclosure.

FIG. 1 is a schematic diagram of an exemplary laser treatment system 100. System 100 may include a laser fiber 102, a laser generator 104 that may generate laser energy 106, and a waveguide 108 optically coupling laser generator 104 to laser fiber 102. It is contemplated that laser fiber 102 and waveguide 108 may be parts of a singular elongate member, or alternatively, different parts joined together. Laser fiber 102 and waveguide 108 may be cylindrical. System 100 also may include a probe 110, in which at least a distal end of laser fiber 102 may be supported. Laser energy 106 may be discharged from a distal end of laser fiber 102 at a targeted material within a subject, as part of a treatment or other medical procedure. Examples of treatments/medical procedures may include tissue ablation; fragmentation of kidney, ureteral, or bladder calculi; and/or fragmentation of kidney, ureteral, or bladder stones.

Figure 2:
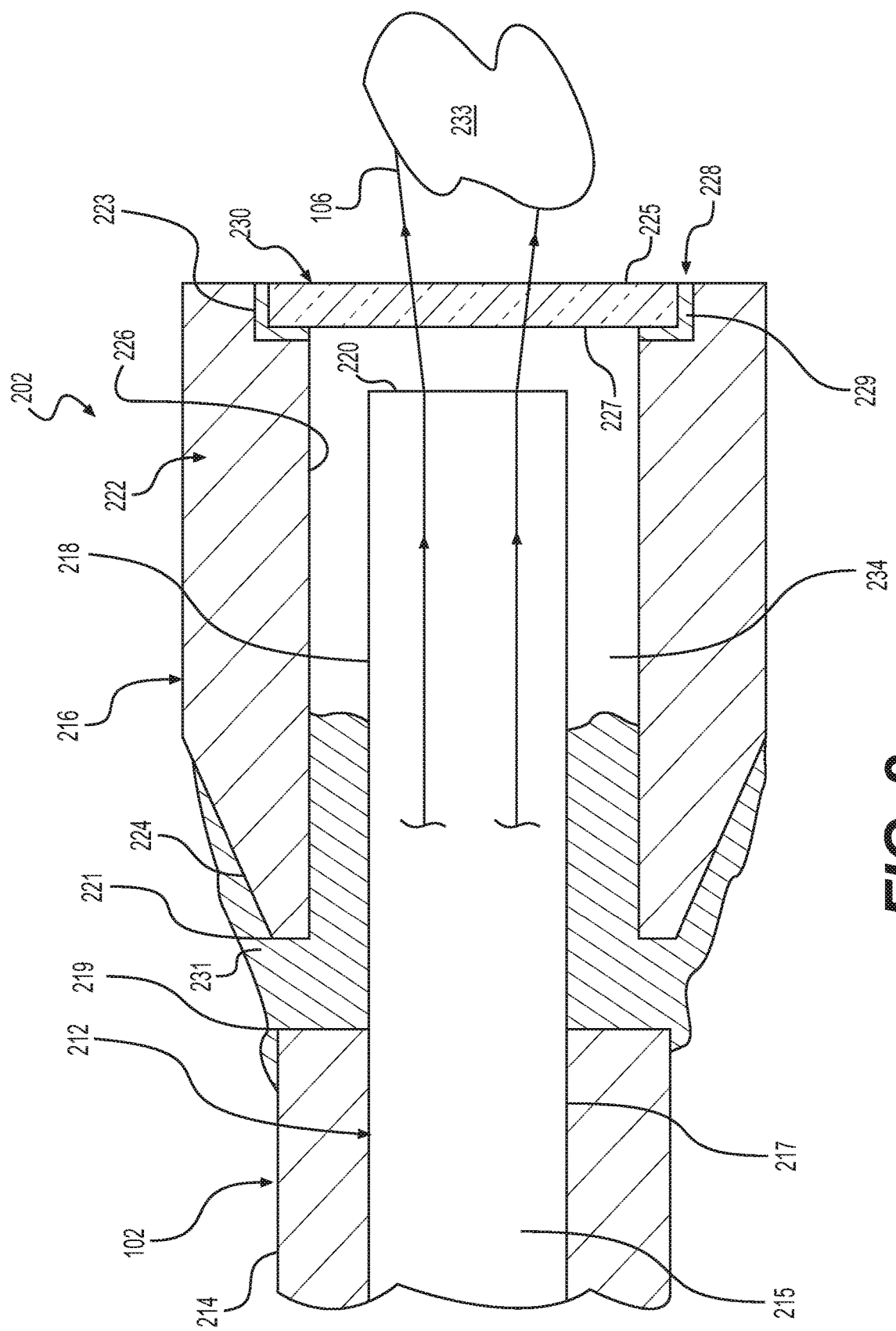
FIG. 2 shows a cross-sectional view of a laser fiber, in accordance with aspects of the present disclosure.

FIG. 2 shows a cross-sectional view of laser fiber 102, and in particular, a distal end 202 of laser fiber 102. Laser fiber 102 may include an optical fiber 212, a covering 214, and a fiber tip 216. Optical fiber 212 may include, for example, a central core 215, with at least a portion of central core 215 being surrounded by a concentric cladding 217. Central core 215 may be at least partially formed of silica (e.g., quartz glass, amorphous silicon dioxide, or any other similar light transmissive materials), either in pure form or including one or more dopants. Cladding 217 may be made of a material that has a lower refractive index than central core 215 to assist with confining laser energy to central core 215. This may facilitate the delivery of laser energy 106 through central core 215 via total internal reflection within central core 215. Optical fiber 212 may include a distal portion 218 terminating at a distal end face 220. Laser energy 106 may be emitted from distal end face 220 toward a targeted material 233.

Covering 214 may include one or more concentric layers of material surrounding optical fiber 212. For example, covering 214 may include a polymer jacket or sheath surrounding cladding 217. The polymer jacket or sheath may be made of acrylate. Additionally or alternatively, covering 214 may include a buffer layer made of resin. Covering 214 may offer mechanical protection and/or support to optical fiber 212. A distal end 219 of covering 214 may be proximal distal portion 218 of optical fiber 212, such that distal portion 218 may protrude distally from distal end 219 of covering 214.

Distal portion 218 of optical fiber 212 may be encased within, surrounded by, or otherwise received within fiber tip 216. Fiber tip 216 may be configured to protect distal portion 218. For example, fiber tip 216 may prevent or reduce damage to distal portion 218 that would otherwise occur due to contact between distal portion 218 and targeted material 233, and/or due to close proximity of distal portion 218 to targeted material 233, during treatment.

Fiber tip 216 may include a tubular member 222. Tubular member 222 may include, for example, a fused silica tube. Tubular member 222 may include a proximal portion 224 with an outer diameter that decreases along a proximal direction. The outer diameter of tubular member 222 may, for example, taper down as tubular member 222 approaches covering 214. The change in outer diameter may result in a proximal end 221 of tubular member 222 having an outer diameter substantially equal to an outer diameter of distal end 219 of covering 214.

Tubular member 222 may include a passage 226 terminating at an opening 228. Opening 228 may be covered by a shielding member 230. Shielding member 230 may be a circular window. Shielding member 230 may have a distal-facing surface 225 and a proximal-facing surface 227. Shielding member 230 may be made of, for example, a chemically-strengthened aluminosilicate sheet glass, such as GORILLA GLASS, GORILLA GLASS 2, GORILLA GLASS 3, or GORILLA GLASS 4 from CORNING. An exemplary composition may include an alkali aluminosilicate glass having 66.4 mol % $SiO_2$; 10.3 mol % $Al_2O_3$; 0.60 mol % $B_2O_3$; 4.0 mol % $Na_2O$; 2.10 mol % $K_2O$; 5.76 mol % MgO; 0.58 mol % CaO; 0.01 mol % $ZrO_2$; 0.21 mol % $SnO_2$; and 0.007 mol % $Fe_2O_3$.

The chemical strengthening may include strengthening by ion exchange. Sheet glass material may be immersed in a molten alkaline potassium salt at a high temperature, wherein smaller sodium ions in the sheet glass material may be replaced by larger potassium ions from the salt bath. Because the larger potassium ions occupy more volume than the smaller sodium ions, they create a surface layer of high residual compressive stress at distal-facing surface 225 and/or proximal-facing surface 227, leaving material between those surfaces protected and under a reduced tensile stress load. These characteristics provide shielding member 230 with strength (e.g., the ability to withstand an applied load without failure or plastic deformation), an ability to contain flaws, and overall crack-resistance beyond that of other glass materials. The strength of shielding member 230 may, for example, exceed that of tubular member 222 and/or distal portion 218 of optical fiber 312. Accordingly, shielding member 230 may be highly resistant to being damaged. Alternatively, shielding member 230 may include any other suitable strengthened, toughened, or reinforced sheet glass. Shielding member 230 may be stronger and/or tougher than distal portion 218 of optical fiber 212 and/or tubular member 222.

In one example, a recess 232 may be formed in a distal end face 223 of tubular member 222. Recess 232 may be annular, and may extend around passage 226. Recess 232 may receive shielding member 230. Recess 232 may be sized such that distal-facing surface 225 of shielding member 230 may be substantially flush with distal end face 223 of tubular member 222. Alternatively, shielding member 230 may cover the entirety of distal end face 223.

Shielding member 230 may be coupled to tubular member 222 using an epoxy 229 or any other suitable adhesive. Tubular member 222 also may be coupled to covering 214 and/or distal portion 218 of optical fiber 212 by an epoxy 231 or any other suitable adhesive. Epoxy 229 and/or epoxy 231 may be introduced in liquid form, and may be cured thereafter by exposure to ultraviolet light.

Fiber tip 216 may form a sealed cavity 234 around distal portion 218 of optical fiber 212. Sealed cavity 234 may be filled, for example, with air. Distal portion 218 of optical fiber 212 may be centered within sealed cavity 234 and/or tubular member 222, such that a predetermined distance or spacing is provided between an interior surface of tubular member 222 and an exterior surface of optical fiber 212. Additionally or alternatively, distal end face 220 of optical fiber 212 may be spaced from proximal-facing surface 227 of shielding member 230. Predetermined distances or spacing may be set to alleviate or otherwise limit damage to distal portion 218 of optical fiber 212 during use, manipulate (e.g., focus or diffuse) a shock wave generated during use, and/or improve ablation efficiency. According to one exemplary usage, shielding member 230 may be positioned in contact with targeted material 233, or at a distance about 2 mm or less from material 233. Even at such a close range, the physical properties of shielding member 230 may allow it to remain capable of protecting distal portion 218 of optical fiber 212 from being damaged.

Laser energy 106 may be produced by laser generator 104 (FIG. 1). Laser generator 104 may include one or more laser sources, such as laser resonators, that produce laser energy 106. In one example, laser generator 104 may produce laser energy 106 in the form of a pulse train or continuous wave. Laser generator 104 may include Q-switched laser rods to produce laser energy 106, such as, for example, a holmium doped yttrium aluminum garnet (Ho:YAG) laser rod, a thulium doped yttrium aluminum garnet (Tm:YAG) laser rod, or other laser rod suitable for producing laser energy 106. Laser energy 106 may have a power of approximately 1-50 W, a pulse repetition frequency of about 1 to about 2000 Hz, and an energy level of about 1 mJ to about 5 J. While some examples are described here, it should be understood that laser energy 106 having other parameters also may be used. It is contemplated that distal end face 220 of optical fiber 212 and/or proximal-facing surface 227 of shielding member 230 may be coated with an anti-reflective coating to enhance transmission of laser energy 106 by distal end face 220 and/or proximal-facing surface 227. Alternatively, the anti-reflective coating may be omitted as long as the resulting reduction in transmission is acceptable to the user.

Figure 3:
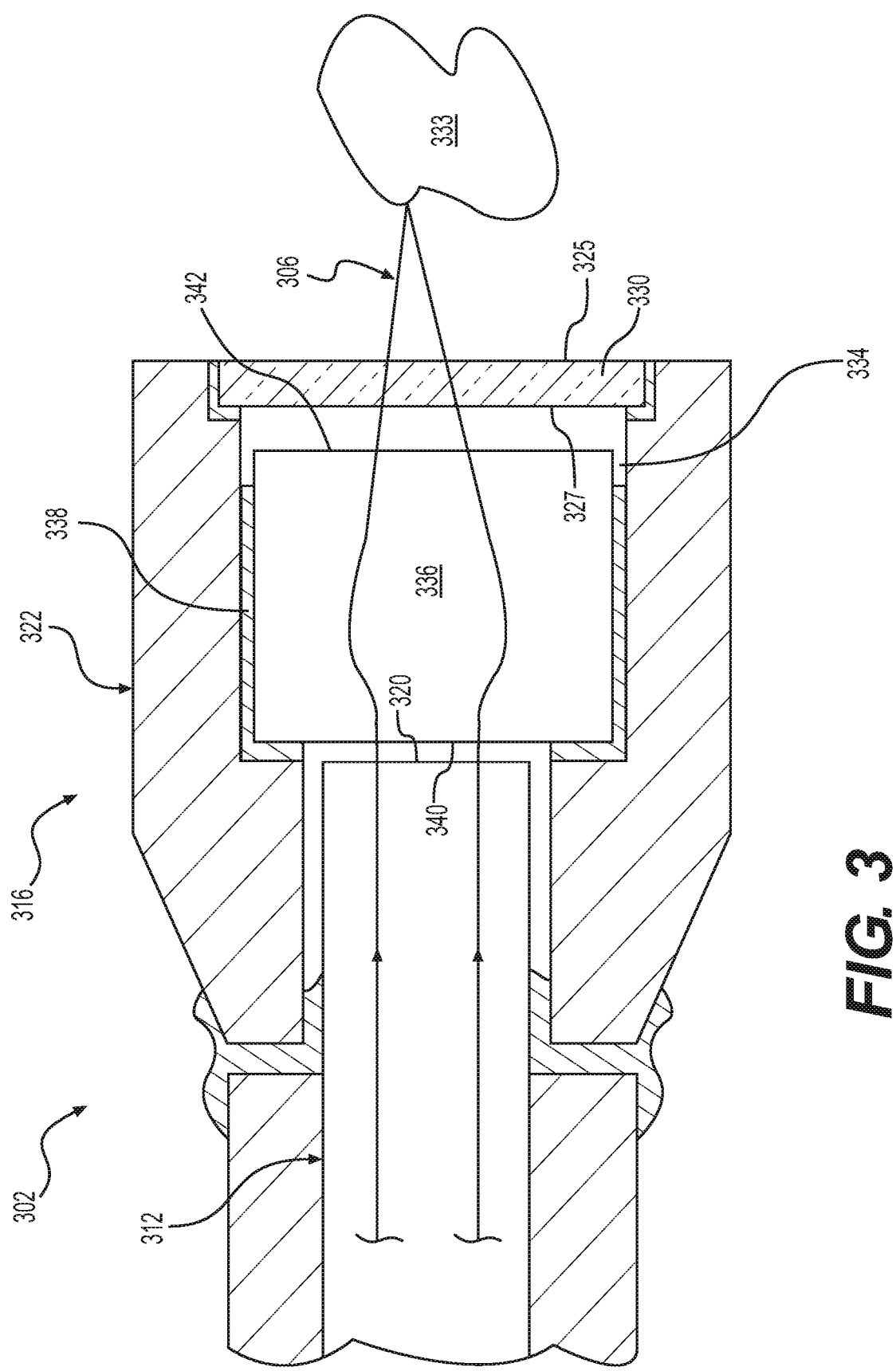
FIG. 3 shows a cross-sectional view of another laser fiber, in accordance with aspects of the present disclosure.

FIG. 3 shows a cross-sectional view of a distal end of another laser fiber 302. Laser fiber 302 may be used in laser treatment system 100 (FIG. 1). For example, laser fiber 302 may replace laser fiber 102 or laser fiber 102 (FIG. 2). Laser fiber 302 may include an optical fiber 312 and a fiber tip 316 similar to corresponding components of laser fiber 102. It is contemplated that laser fiber 302 may be nearly identical to laser fiber 102. Some of the components of laser fiber 302 that are not numbered and/or are not described here may correspond to similar components of laser fiber 102, and descriptions of those components are not reiterated here for the sake of brevity. A similar approach has been taken with respect to the other figures that will be described below.

One difference between laser fibers 102 and 302 is that laser fiber 302 may include a lens member 336. Lens member 336 may be received within a tubular member 322 of fiber tip 316. For example, lens member 336 may be positioned within a proximal portion of a sealed cavity 334 between a distal end face 320 of optical fiber 312 and a proximal-facing surface 327 of a shielding member 330 of fiber tip 316. Lens member 336 may be secured to an interior surface of tubular member 322 by an epoxy 338, which may be one cured by exposure to ultraviolet light. Additionally or alternatively, lens member 336 may be secured to proximal-facing surface 327 by a similar or identical epoxy (not shown).

Lens member 336 may include, for example, a gradient index lens. Gradient index lenses may feature plane optical surfaces (e.g., optical surfaces 340 and 342) and may achieve focus via a substantially continuous change of the refractive index within the lens material instead of through the use of curved optical surfaces. As such, gradient index lenses may be suited for use in assemblies where a lens should have a specific working distance. It is contemplated that lens member 336 may be selected from a number of gradient index lenses that have similar or identical shapes, but different optical properties based on their refractive index profiles.

In one example, lens member 336 may have a positive focusing power such that it may condense laser energy 306. This may result in more laser energy 306 being concentrated on a smaller area of a targeted material 333. The concentration of laser energy 306 may increase the overall energy delivered to targeted material 333, thereby speeding up treatment times, allowing harder materials to be broken down, and/or giving the user precise control over aiming of laser energy 306. It is contemplated that the refractive index gradient of lens member 336 may be selected to set a focal length, such that laser energy 306 may be focused a predetermined distance from a distal-facing surface 325 of shielding member 330. The predetermined distance may be, for example, about 2 mm or less from distal-facing surface 325. The predetermined distance may be increased or decreased as desired. Increasing the distance may decrease the likelihood of optical fiber 312 and/or lens member 336 being damaged during use, while decreasing the distance may increase a power of the emitted laser energy 306.

Additionally or alternatively, lens member 336 may be configured to influence laser energy 306 in other ways. For example, lens member 336 may have a refractive index gradient that may result in a negative focusing effect, such that lens member 336 may disperse laser energy 306 as laser energy 306 is emitted. In other words, lens member 336 may have the effect of a concave lens. This may be useful when using laser energy 306 to ablate tissue. It is also contemplated that lens member 336 may have a refractive index gradient that may cause the emission of laser energy 306 at an angle relative to a central longitudinal axis of lens member 336. This may, for example, allow laser energy 306 to be directed at target areas/materials that may not be accessible to the proximal end face of laser fiber 302.

Figure 4:
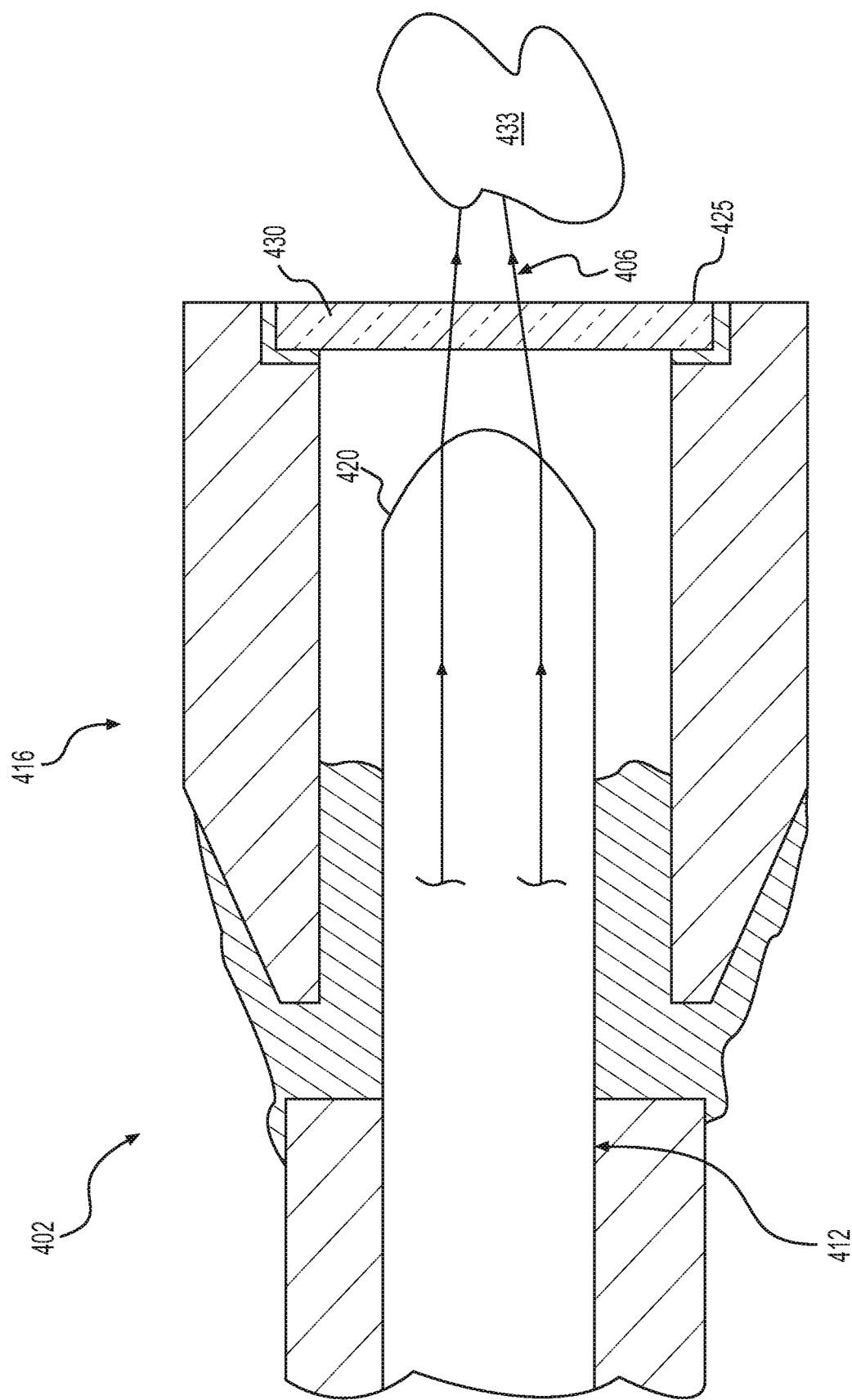
FIG. 4 shows a cross-sectional view of yet another laser fiber, in accordance with aspects of the present disclosure.

FIG. 4 shows a cross-sectional view of a distal end of another laser fiber 402. Laser fiber 402 may be used in laser treatment system 100 (FIG. 1). For example, laser fiber 402 may replace any of laser fibers 102 and 302. It is contemplated that laser fiber 402 may be nearly identical to any of the aforementioned laser fibers. Laser fiber 402 may include an optical fiber 412 and a fiber tip 416, each of which may be similar to any of the aforementioned optical fibers and fiber tips, respectively. One difference is that optical fiber 412 may have a shaped distal end face 420. The shaping may allow distal end face 420 to act as a lens or collimator useful for controlling, for example, Fresnel loss, depth of focus, convergence/divergence of laser energy 406, and spot size of laser energy 406 emitted by optical fiber 412, without requiring mounting a separate lens or other member at or near distal end face 420.

As shown in FIG. 4, distal end face 420 may be sculpted to be convex rather than flat, allowing distal end face 420 to act as a convex lens. As such, distal end face 420 may have a positive focusing power such that it may condense laser energy 406 as laser energy 406 is emitted. This may result in more laser energy 406 being concentrated on a smaller area of targeted material 433. The concentration of laser energy 406 may increase the overall energy delivered to the targeted material 433, thereby speeding up treatment times, allowing harder materials to be processed, and giving the user precise control over aiming of laser energy 406. It is contemplated that the shape of distal end face 420 may be selected to set a focal length of distal end face 420, such that laser energy 406 may be focused a predetermined distance from distal end face 420. The predetermined distance may be, for example, about 2 mm or less from a distal-facing surface 425 of a shielding member 430 of fiber tip 416. The predetermined distance may be increased or decreased as desired. Increasing the distance may decrease the likelihood of optical fiber 412 being damaged during use, while decreasing the distance may increase a power of the emitted laser energy 406. While shaping distal end face 420 may weaken the distal end of optical fiber 412 by, for example, thinning the distal tip of optical fiber 412, the protection afforded by shielding member 430 may protect the distal tip, thereby compensating for any weakness.

Additionally or alternatively, optical fiber 412 may be shaped to achieve other effects. For example, a distal end portion may include a down-taper (not shown), which may decrease the spot size of emitted laser energy 406 and/or increase divergence. It is also contemplated that distal end face 420 may have a concave shape, thereby acting as a concave lens for increasing the divergence of emitted laser energy 406. It is also contemplated that distal end face 420 may be flat, but angled, to redirect laser energy 406 sideways, or at least at an angle that may reduce back reflection associated with distal end face 420.

Figure 5:
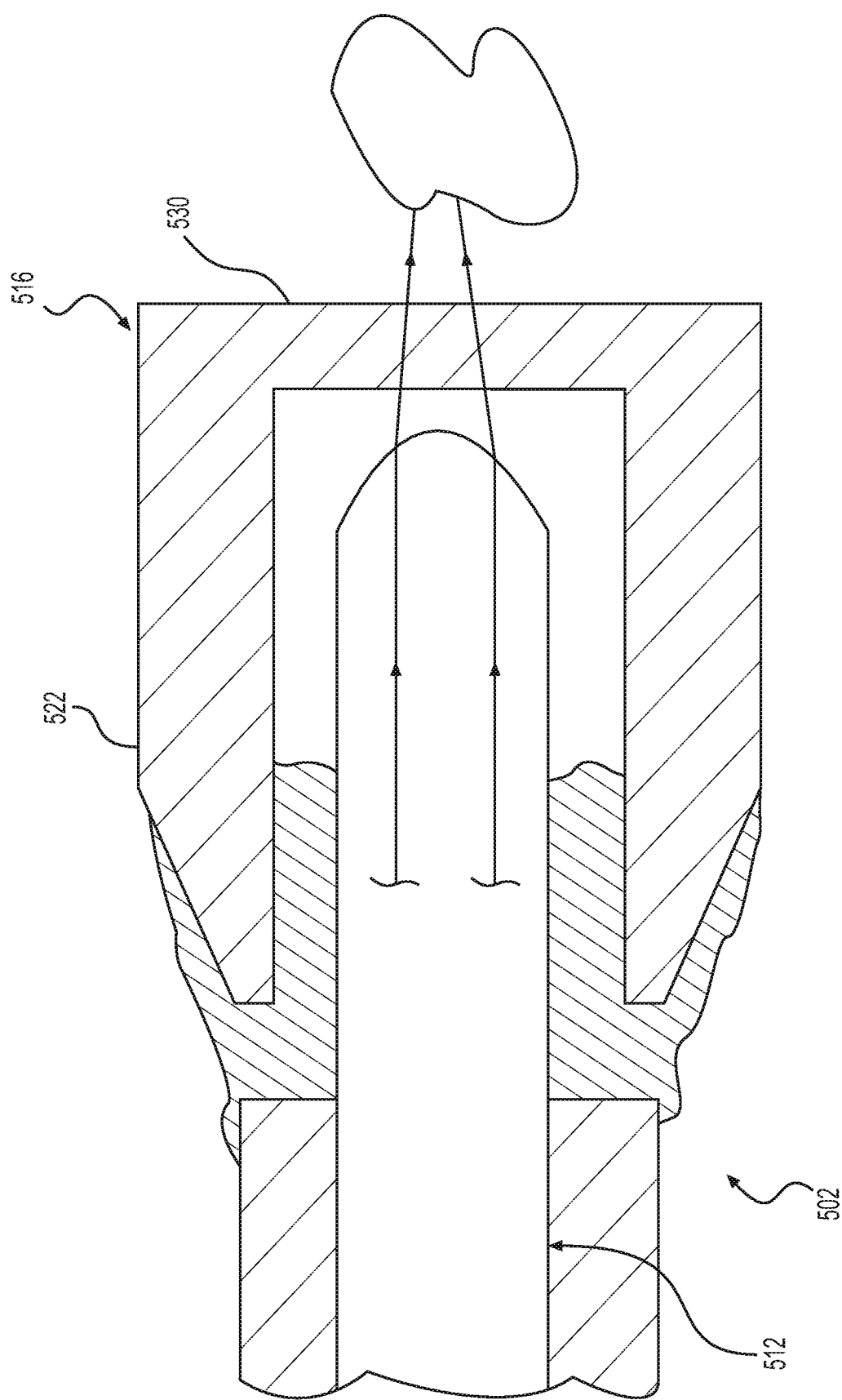
FIG. 5 shows a cross-sectional view of yet another laser fiber, in accordance with aspects of the present disclosure.

FIG. 5 shows a cross-sectional view of a distal end of another laser fiber 502. Laser fiber 502 may be used in laser treatment system 100 (FIG. 1). For example, laser fiber 502 may replace any of the aforementioned laser fibers. Laser fiber 502 may include an optical fiber 512 similar to any of the aforementioned optical fibers. It is contemplated that optical fiber 512 may be, for example, identical to optical fiber 412. Laser fiber 502 may differ from the aforementioned laser fibers in that a fiber tip 516 of laser fiber 502 may have a singular or monolithic construction. Each of fiber tips 216, 316, and 416 may be constructed by coupling a shielding member to a tubular member. Fiber tip 516, on the other hand, may be one continuous piece having a tubular portion 522 and a shielding portion 530. Tubular portion 522 and shielding portion 530 may be made of the same material as shielding member 130, but may be manufactured in a manner that forms the material into a three-dimensional shape, rather than a planar or plate-like shape. Alternatively, a multi-part fiber tip also is contemplated, similar to fiber tips 216, 316, and 416, where shielding members 130, 230, and 330 may be replaced with a curved (e.g., at least partially convex or concave) or other three-dimensionally shaped shielding member.

As shown in laser treatment system 100 of FIG. 1, waveguide 108 may include a connector 140 at its proximal end. Connector 140 may be removably coupled to laser generator 104. Laser generator 104 may include, for example, a connector coupler (not shown) for removably coupling with connector 140. The connector coupler may include a Subminiature version A (SMA) coupler. The coupler may include a plate-like proximal base portion, and an externally-threaded cylindrical portion extending distally from the base portion. Laser generator 104 may generate laser energy 106 in the form of a laser beam that may be directed down a center of the coupler.

Figure 6:
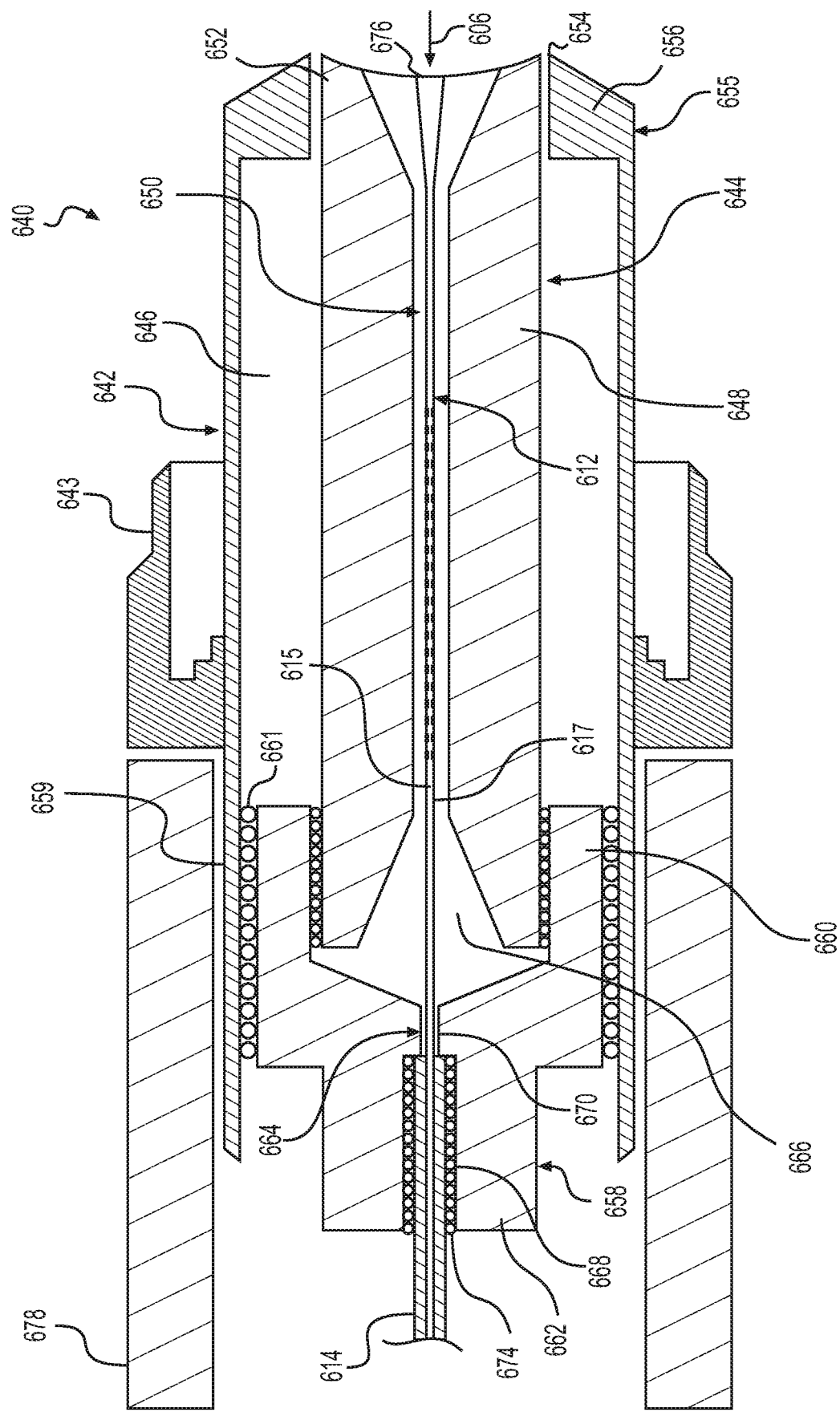
FIG. 6 shows a cross-sectional view of a laser fiber connector, in accordance with aspects of the present disclosure.

Aspects of an exemplary connector 640, which may be used as connector 140, are shown in FIG. 6. Connector 640 may include a coupler 642 having an internally-threaded nut 643. Coupler 642 may be, for example an SMA coupler complementary to the SMA coupler of laser generator 140. Coupler 642 may be made of stainless steel or any other suitable material. Coupler 642 may be screwed onto and screwed off of the coupler of laser generator 104 for attaching connector 640 to and detaching connector 640 from laser generator 104.

Connector 640 may include a ferrule 644. Ferrule 644 may be made of silica or any other suitable material. Ferrule 644 may be received in a cavity 646 of coupler 642. Ferrule 644 may be centered relative to coupler 642 in cavity 646. Ferrule 644 may be an elongate hollow body 648 having a passage 650 extending therethrough into which is inserted a proximal end 650 of an optical fiber 612. Optical fiber 612 may be similar to any of the aforementioned optical fibers. Passage 650 may include a down-taper at a proximal end, and an up-taper at a distal end. A proximal end 652 of ferrule 644 may be supported in an opening 654 in a flange 656 at a proximal end 655 of ferrule 644.

Connector 640 also may include a holder 658. Holder 658 may be made of aluminum or any other suitable material. Holder 658 may include a proximal portion 660 and a distal portion 662. Proximal portion 660 may have a larger diameter than distal portion 662. Proximal portion 660 may be coupled to a distal end 659 of coupler 642 by an epoxy 661 or any other suitable adhesive.

A distal end 656 of ferrule 644 may be supported by holder 658. Holder 658 may be hollow, and may have a passage 664 extending therethrough. Passage 664 may have a proximal region 666, a distal region 668, and an intermediate region 670 between proximal and distal regions 666 and 668. Proximal region 666 may be in proximal portion 660, and may have a larger diameter than intermediate and distal regions 668 and 670. Proximal region 660 may receive distal end 656 of ferrule 644. In one example, an outer surface of distal end 656 may be adhered to an inner surface of proximal portion 660 by an epoxy 672 or other suitable adhesive. Epoxy 672 may include a novolac epoxy resin, such as one that contains epoxy phenol novolac, like EPO-TEK 353ND from EPOXY TECHNOLOGY. Intermediate region 670 may have a smaller diameter than proximal and distal regions 666 and 668, and may receive optical fiber 612. Covering 614 may not be present around the portion of optical fiber 612 in intermediate region 670, or around portions of optical fiber 612 proximal to intermediate region 670. Distal region 668 may be in distal portion 662, and may have a smaller diameter than proximal region 666 and a larger diameter than intermediate region 670. Distal region 668 may receive a portion of a laser fiber 602 that includes optical fiber 612 and a covering 614 concentrically surrounding optical fiber 612. The portion of laser fiber 602 may be seated in distal region 668 and held in place by use of an epoxy 674 or other suitable adhesive. Epoxy 674 may have a lower thermal conductivity than epoxy 661. Accordingly, heat generated in holder 658 may transfer more readily through epoxy 661 and into coupler 642 than through epoxy 674 and to covering 614.

An extension sleeve 678 may surround a distal portion of coupler 642. Extension sleeve 678 may be press-fit onto the distal portion of coupler 642. Extension sleeve 678 may be made of, for example, aluminum.

Laser energy 606 may be directed into optical fiber 612 at a proximal end 676 of optical fiber 612. Laser energy 606 may travel distally through optical fiber 612 and through coupler 642, ferrule 644, and holder 658, on its way to a distal end (not shown) of optical fiber 612, for emission from the distal end onto a targeted material (not shown).

In some instances, laser generator 104 (FIG. 1) may typically be used to provide laser energy 106 to a laser fiber having a fiber core with a particular diameter, or a diameter within a particular range of diameters. However, in order to perform procedures in areas of a subject that may be difficult to access, the user may disconnect the laser fiber from laser generator 104, and may connect a laser fiber having a central core with a smaller diameter. In such a scenario, laser energy 106 launched from laser generator 104 may be too large for the smaller central core. As a result, some laser energy may couple into the cladding surrounding the smaller central core. Then, when the laser fiber is bent to access the target area, the laser energy in the cladding may leak into the covering surrounding the optical fiber. The covering, which may include, for example, acrylate, may absorb the leaked laser energy and generate heat. The covering and the optical fiber, when heated, may expand at different rates. An acrylate coating, for example, may expand about 200 times faster than a fused silica fiber core with cladding. The covering may break due to the stress along the longitudinal axis of the laser fiber. When the temperature rises to about 260 degrees Celsius, an acrylate coating may decompose. When the acrylate coating is broken (e.g., due to mechanical stress and/or thermal decomposition), there may be insufficient tensile protection on the optical fiber, and the optical fiber my break. This is one reason laser fibers that have smaller diameter cores may have a higher failure rate than other laser fibers.

Connector 640 (FIG. 6) may be configured to address one or more of the above-described issues. Optical fiber 612 may include a central core 615 and concentric cladding 617, with central core 615 having a diameter similar to that of the aforementioned smaller fiber core. Cladding 617 on a portion of optical fiber 612 may be removed. For example, cladding 617 may be diffused using a carbon dioxide laser. The portion of optical fiber 612 with diffused cladding 617 may be inserted into passage 650 of ferrule 644, and may be fused with ferrule 644 using the carbon dioxide laser in a manner similar to that associated with BLACK HOLE TECHNOLOGY of AMERICAN MEDICAL SYSTEMS. A length of the portion of optical fiber 612 may be less than a length of passage 650. For example, the portion of optical fiber 612 may be bordered on its proximal and distal sides by portion of optical fiber 612 with full cladding 617. The portions with full cladding 617 may also be received in passage 650.

Due to the disparity in size between laser energy 106 launched from laser generator 104, and the diameter of central core 615, some laser energy 106 may leak into cladding 617. When laser energy 1096 travels along the diffused cladding 617, it may diffuse out of the diffused cladding 617, and may be dissipated as heat. The heat may be absorbed by ferrule 644, coupler 642, holder 658, and/or extension sleeve 678. Epoxy 661 may have a higher thermal conductivity than epoxy 674, to help facilitate heat transfer from holder 658 into coupler 642 and extension sleeve 678, instead of from holder 658 into covering 614. With this design, laser energy in cladding 617 may be dissipated by connector 640 (as heat) before the laser energy reaches covering 614. Since less heat reaches covering 614, one driving factor in causing breakage of laser fiber 602 during bending may be reduced or eliminated.

It will be apparent to those skilled in the art that various modifications and variations can be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A laser fiber, comprising:
an optical fiber configured to transmit energy, including:
a core,
cladding concentrically surrounding at least a portion of the core,
a distal portion including a covering concentrically surrounding the cladding, and
a proximal portion free of the covering, at least a portion of the cladding at the proximal portion being diffused; and
a connector configured to couple the optical fiber to a laser generator, the connector including:
a tubular member having a passage that receives the proximal portion of the optical fiber,
a holder having a passage that (i) receives the tubular member, such that the holder concentrically surrounds a portion of the tubular member, and (ii) receives the distal portion of the optical fiber, and
a coupler concentrically surrounding the tubular member, the proximal portion of the cladding being diffused allowing laser energy in the cladding to leave the optical fiber and convert into heat energy within the tubular member, with at least some of the heat energy being dissipated by the tubular member, holder, and coupler before reaching the distal portion of the optical fiber.

2. The laser fiber of claim 1, further including a first epoxy coupling the distal portion of the optical fiber to the holder.

3. The laser fiber of claim 2, further including a second epoxy coupling the holder to the coupler.

4. The laser fiber of claim 3, wherein the first epoxy has a lower thermal conductivity than the second epoxy.

5. The laser fiber of claim 1, wherein the cladding comprises a material having a lower refractive index than a refractive index of the core.

6. The laser fiber of claim 1, wherein the covering includes a buffer layer comprising resin.

7. The laser fiber of claim 1, wherein the passage of the tubular member includes a down taper at a proximal portion of the tubular member and an up taper at a distal portion of the tubular member.

8. The laser fiber of claim 1, wherein a proximal portion of the holder has a larger inner diameter than an inner diameter of a distal portion of the holder.

9. The laser fiber of claim 8, wherein an intermediate portion of the holder has a smaller inner diameter than the inner diameter of the proximal portion and the inner diameter of the distal portion.

10. The laser fiber of claim 1, further including a third epoxy coupling a distal portion of the tubular member to a proximal portion of the holder.

11. The laser fiber of claim 10, wherein the third epoxy includes a novolac epoxy resin.

12. The laser fiber of claim 4, wherein a proximal portion of the holder is coupled to the coupler via the second epoxy.

13. The laser fiber of claim 1, wherein the connector further includes an extension sleeve, wherein the extension sleeve concentrically surrounds a distal portion of the coupler.

14. The laser fiber of claim 1, wherein a portion of the optical fiber including the diffused cladding is within the passage of the tubular member.

15. A laser fiber, comprising:
an optical fiber including:
a core,
cladding concentrically surrounding at least a portion of the core,
a distal portion including a covering concentrically surrounding the cladding, and
a proximal portion free of the covering, at least a portion of the cladding at the proximal portion being diffused;
a connector removably couplable to a laser generator, the connector including:
a tubular member having a passage that receives the proximal portion of the optical fiber including the portion of the cladding that is diffused, and wherein the passage includes a proximal opening configured to receive laser energy and direct the laser energy into the optical fiber, wherein the distal portion of the optical fiber including the covering is distal to the tubular member,
a holder having a passage that (i) receives the tubular member, such that the holder concentrically surrounds a portion of the tubular member, and (ii) receives the distal portion of the optical fiber, and
a coupler concentrically surrounding the tubular member;
a first epoxy coupling the distal portion of the optical fiber to the holder; and
a second epoxy coupling the holder to the coupler, wherein the first epoxy has a lower thermal conductivity than the second epoxy.

16. The laser fiber of claim 15, wherein a portion of the optical fiber including the diffused cladding is within the passage of the tubular member.

17. The laser fiber of claim 15, wherein the cladding comprises a material having a lower refractive index than a refractive index of the core.

18. The laser fiber of claim 15, further including a third epoxy coupling a distal portion of the tubular member to a proximal portion of the holder.

19. A laser fiber, comprising:
an optical fiber including:
a core, and
cladding concentrically surrounding at least a portion of the core, wherein at least a portion of the cladding is diffused, and the cladding comprises a material having a lower refractive index than a refractive index of the core; and
a connector removably couplable to a laser generator, the connector including:
a tubular member having a passage that receives a proximal portion of the optical fiber, wherein the passage of the tubular member includes a down-taper at a proximal end of the passage,
a holder having a first passage that receives the tubular member and a proximal portion of the optical fiber, and a second passage that that receives a distal portion of the optical fiber, the first passage and the second passage separated by an intermediary passage of a smaller diameter than both the first passage and the second passage, and
a coupler concentrically surrounding the tubular member, wherein a portion of the optical fiber including the portion of the diffused cladding that is diffused is within the passage of the tubular member.

20. The laser fiber of claim 1, the distal portion comprising a distal tip, the distal tip including a sheet glass material having a chemically strengthened surface layer.

* * * * *